United States Patent [19]
Yum et al.

[11] Patent Number: 5,104,390
[45] Date of Patent: * Apr. 14, 1992

[54] FLUID RECEIVING RECEPTACLE COMPRISING BIOCIDE DELIVERY SYSTEM CONTACTING OUTSIDE OF RECEPTACLE

[75] Inventors: Su Il Yum; Felix Theeuwes, both of Los Altos, Calif.

[73] Assignee: ALZA Corporation, Palo Alto, Calif.

[*] Notice: The portion of the term of this patent subsequent to Nov. 13, 2007 has been disclaimed.

[21] Appl. No.: 503,017

[22] Filed: Apr. 2, 1990

Related U.S. Application Data

[63] Continuation-in-part of Ser. No. 239,563, Sep. 1, 1988, Pat. No. 4,938,748.

[51] Int. Cl.⁵ .............................. A61M 1/00
[52] U.S. Cl. .................... 604/323; 604/890.1
[58] Field of Search ........... 604/890.1, 892.1, 265, 604/317, 322–327, 80–85

[56] References Cited

U.S. PATENT DOCUMENTS

| | | | |
|---|---|---|---|
| 3,312,221 | 4/1967 | Overment | 604/323 |
| 3,468,471 | 9/1969 | Linder | 422/294 |
| 4,144,309 | 3/1979 | Langston et al. | 422/305 |
| 4,193,403 | 3/1980 | Langston et al. | 128/275 |
| 4,233,263 | 11/1980 | Schaeffer | 422/28 |
| 4,236,517 | 12/1980 | Langston et al. | 128/275 |
| 4,241,733 | 12/1980 | Langston et al. | 128/275 |
| 4,392,848 | 7/1983 | Lucas et al. | 604/265 |
| 4,418,038 | 11/1983 | Theeuwes | 422/37 |
| 4,432,754 | 2/1984 | Urquhart et al. | 604/85 |
| 4,445,889 | 5/1984 | Wong et al. | 604/49 |
| 4,455,145 | 6/1984 | Theeuwes | 604/892 |
| 4,460,367 | 7/1984 | Wong et al. | 604/890 |
| 4,464,258 | 8/1984 | Wong et al. | 210/205 |
| 4,505,703 | 3/1985 | Gale et al. | 604/317 |
| 4,511,353 | 4/1985 | Theeuwes | 604/85 |
| 4,529,398 | 7/1985 | Wong et al. | 604/49 |
| 4,601,880 | 7/1986 | Wong et al. | 422/28 |
| 4,728,498 | 3/1988 | Theeuwes | 422/29 |
| 4,740,201 | 4/1988 | Theeuwes et al. | 604/85 |
| 4,871,352 | 10/1989 | Tran | 604/82 |
| 4,969,871 | 11/1990 | Theeuwes et al. | 604/892.1 |

FOREIGN PATENT DOCUMENTS 239563  10/1984  World Int. Prop. O. .

*Primary Examiner*—Randall L. Green
*Assistant Examiner*—K. Reichle
*Attorney, Agent, or Firm*—Paul L. Sabatine; Jacqueline S. Larson; Edward L. Mandell

[57] ABSTRACT

A patient-care apparatus comprising a container for receiving a biological fluid, and a delivery device on the outside of the container, which device comprises a biocide that is released to the container for preventing the multiplication of and/or eliminating the presence of unwanted pathogens in the container.

9 Claims, 4 Drawing Sheets

FLUID RECEIVING RECEPTACLE COMPRISING BIOCIDE DELIVERY SYSTEM CONTACTING OUTSIDE OF RECEPTACLE

CROSS-REFERENCE TO RELATED APPLICATIONS

This application is a continuation-in-part of U.S. Application Ser. No. 07/239,563 filed on Sep. 1, 1988, now U.S. Pat. No. 4,938,948, issued July 3, 1990 which application Ser. No. 07/239,563 is copending with U.S. Application Ser. No. 07/467,473, filed Jan. 19, 1990, and it is copending with U.S. Application Ser. No. 07/467,478, filed Jan. 19, 1990, now both abandoned. All of these applications are incorporated herein by reference, and benefit is claimed of their filing dates. These references are assigned to the ALZA Corporation of Palo Alto, Calif.

DESCRIPTION OF TECHNICAL FIELD

This invention pertains to a patient-care apparatus comprising, in combination, a container comprising an external biocidal means releasably positioned on the outside wall of the container for delivering a biocide through the wall into the container. More specifically, the invention relates to a urinary drainage container comprising an external source of biocide. The biocide is delivered into the container through at least one wall of the container for preventing and eliminating the presence of unwanted pathogens present inside the container.

DESCRIPTION OF BACKGROUND ART

It is now generally acknowledged that indwelling catheterization in medical, surgical, gynecological, urological and other patients leads to serious infection of the urogenital tract. The process of indwelling catheterization is performed in approximately 10 to 15 percent of hospitalized patients. Despite the use of the most careful aseptic techniques undertaken while the catheter is in the patient, approximately fifty percent of the patients develop an infection when a catheter is in place for twenty-four hours or longer. This is harmful to the patients because they are subjected to the risk of cystitis, acute pyelonephrititis and life-threatening septicemia, which carries a risk of mortality, as reported in *Arch. Internal Med.*, Vol. 110, pp. 703-11, (1962); *Antimicrob. Agents Chemother.*, pp 617-23, (1963); and *Lancet*, Vol. 1, pp. 310-12, (1960).

The occurrence of the above-mentioned infection is encouraged by many circumstances. These circumstances include prolonged use of indwelling Foley catheters often accompanied by the absence of a sterile insertion and maintenance techniques, and by having the catheter connected to a clean, but not sterile drainage collection container placed in the immediate vicinity of the patient's bed. These and other circumstances that predispose a patient to infection are reported in *Urinary Tract Infection And Its Management*, edited by Kaye, D., Chapter 15, "Care of the Indwelling Catheter," pp. 256-66, (1972), published by the C. V. Mosby Company, St. Louis, Mo.; and in "Factors Predisposing To Bacteriuria During Indwelling Urethral Catheterization," *New Eng. J. Med.*, Vol. 291, pp. 215-23, (1974).

Attempts have been made by the prior art to reduce the incidence of catheter acquired infections, to reduce the presence of unwanted organisms in drainage containers, but these attempts have not met with general acceptance. For example, one attempt consists in systemic chemoprophylaxis achieved by orally administering an antibiotic such as chloramphenicol, penicillin or streptomycin. This attempt, however, affords no significant protection against the acquisition of infection after indwelling catherization, as reported in *Arch. Internal Med.*, Vol. 110, pp. 703-11, (1962); *Acta Chiv. Scand.*, Vol. 118, pp. 45-52, (1959); and *Dis. Mon.*, pp. 1-36, (Sep. 1960).

The attempts made by the prior art for preventing or eliminating unwanted organisms also include adding a biocide to the inside of a drainage container, or placing a device inside the container wherein the device releases a biocide. For example, formalin is added to the fluid collection container for controlling, that is, killing pathogens. This method, however, does not enjoy general use because there is a risk of siphoning formalin into the urinary tract, as reported in *British Med. J.*, Vol. 2, pp 4233-25, (1964). In U.S. Pat. No. 4,233,263 the patentee Shaeffer disclosed adding 3% hydrogen peroxide solution to a urine bag for reducing the risk of urinary tract infection. This method is inherently subjected to poor results because of a lack of compliance. That is, each time urine is drained from the urinary drainage bag the hydrogen peroxide is drained and it must be reintroduced into the bag every 8 hours. This requires mixing and agitation, and it is often accompanied by spilling of the solution. Also, hydrogen peroxide loses its strength over time. In U.S. Pat. Nos. 4,193,403 and 4,241,733 Langston et al disclose a device inside a urinary drainage bag. The device contains paraformaldehyde that depolymerizes to formaldehyde in the presence of moisture inside the drainage bag. While formaldehyde is an antimicrobial, it is not used because it may be injurious to an animal host. In World Intellectual Property Organization Appln. Ser. No. 84/04036 Stupar et al disclosed a urine bag provided with gas generating compounds that are activated by proximity to urine to give a gaseous halogen antimicrobial. This too has not enjoyed acceptance because gaseous halogen compounds are injurious to the mucosal tissues of the unitary tract.

It will be appreciated by those versed in the urinary drainage art that, in view of the above presentation, a critical need exists for a novel and unique means for introducing a biocidal agent into a urinary drainage system. The need exists for an acceptable and workable means for introducing a biocide into a urinary drainage system and the need also exists for overcoming the difficulties associated with the prior art use of an internal biocide and an internal delivery device. It will be further appreciated that a pressing need exists for a biocidal delivery means that is not introduced into the urinary container, but can provide a biocidal agent from an external delivery source in contact with the outside of the drainage container.

DISCLOSURE OF OBJECTS OF THE INVENTION

Accordingly, it is an immediate object of this invention to provide an improvement in preventing, eliminating and reducing the presence of unwanted infectious organisms in a urinary drainage collection system, which improvement comprises a biocidal delivery means that overcomes the disadvantages associated with the prior art.

It is a further object of the invention to provide a drainage collection system comprising, in combination, a urine receiving container and means for positioning on the exterior of the container for delivering a biocide that enters through a wall of the container for preventing the multiplication of and/or the elimination of pathogens in the container.

Another object of the invention is to provide a delivery device that is permanently or releasably mounted on the exterior of the urine receiving container for delivering a biocidal agent from the exterior into the container.

Another object of the invention is to provide a urinary drainage container with an external detachable dispensing device that releases an antipathogenic agent, and which detachable dispensing device embraces inventive simplicity, is inexpensive to make and, is disposable.

Another object of the invention is to provide a combination comprising a fluid receiving container and a delivery device positioned on the outside of the container, which delivery device comprises a biocide and a flux enhancer for increasing the amount of biocide that enters the container in unit time.

Another object of the invention is to provide a delivery device for positioning on the external surface of a drainage container, wherein the delivery device comprises a shape that corresponds to the shape of the external surface of the container.

Another object of the invention is to provide a detachable pouch for positioning on the outside wall of a urinary drainage container, and which pouch contains a biocide that passes through the wall into the container for preventing bacterial contamination within the container.

Another object of the invention is to provide a biocidal delivery device that can be permanently or releasably mounted on the outside wall of a urinary drainage container, and which delivery device can be used once a day, twice a day, or the like, or which delivery device can be used for up to 480 hours or longer.

Another object of the invention is to provide a delivery device for positioning on the exterior surfaces of a fluid receiving container, which delivery device comprises a composition of matter that is released by the device and diffuses into the wall to increase its permeability to the passage of a biocide.

Another object of the invention is to provide a biocidal delivery device that can be placed on the outside wall of a urinary drainage bag for delivering a biocidally effective amount at a controlled rate over a prolonged period of time for its intended effect.

Another object of the invention is to provide a device that is attached to the exterior surface of a container, and which device releases a plasticizer that permeates into the wall to change the permeability of the wall.

Another object of the invention is to provide a urinary drainage delivery system that introduces a biocide into a container essentially-free of generating a gas in the drainage system.

Another object of the invention is to provide an improvement in a urinary drainage system wherein the improvement comprises positioning a biocidal delivery device on the outside of a drainage system for introducing a biocide into the drainage system.

Another object is to provide a delivery device that attaches to the wall to release a wall modifying composition of matter to facilitate absorption of the delivered biocide.

Another object of the invention is to provide an improved method for preventing and/or eliminating the presence or growth of bacteria in a urinary drainage system wherein the improvement comprises placing a biocidal delivery device on the outside of a urinary container and then delivering a biocide from the device into the container for the intended purpose.

These and other objects of the present invention will become more apparent upon a consideration of the drawings, the specification and the accompanying claims.

BRIEF DESCRIPTION OF THE DRAWING FIGURES

In the drawing figures, which are not drawn to scale, but are set forth to illustrate various embodiments of the invention, the drawing figures are as follows.

Figure 2:
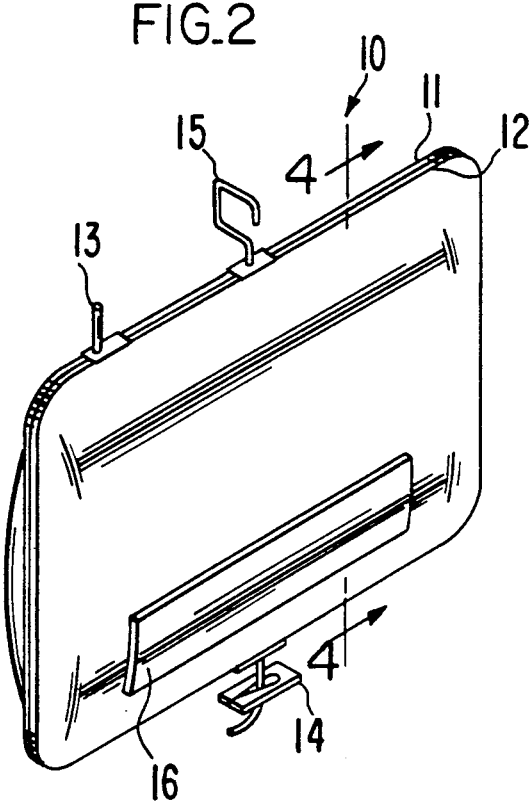
FIG. 2 is a side view of a urinary drainage container with a biocidal dispensing device permanently attached or releasably attached to the container.
Figure 6:
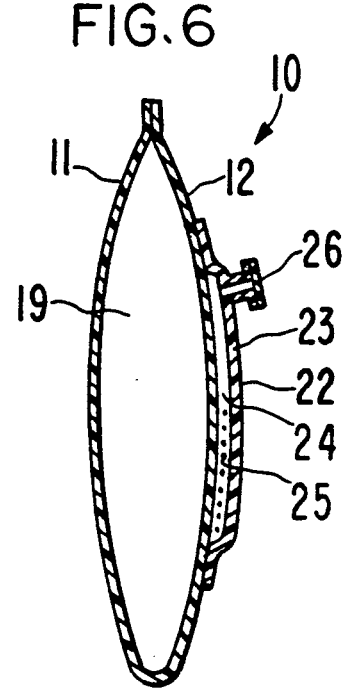
Figure 7:
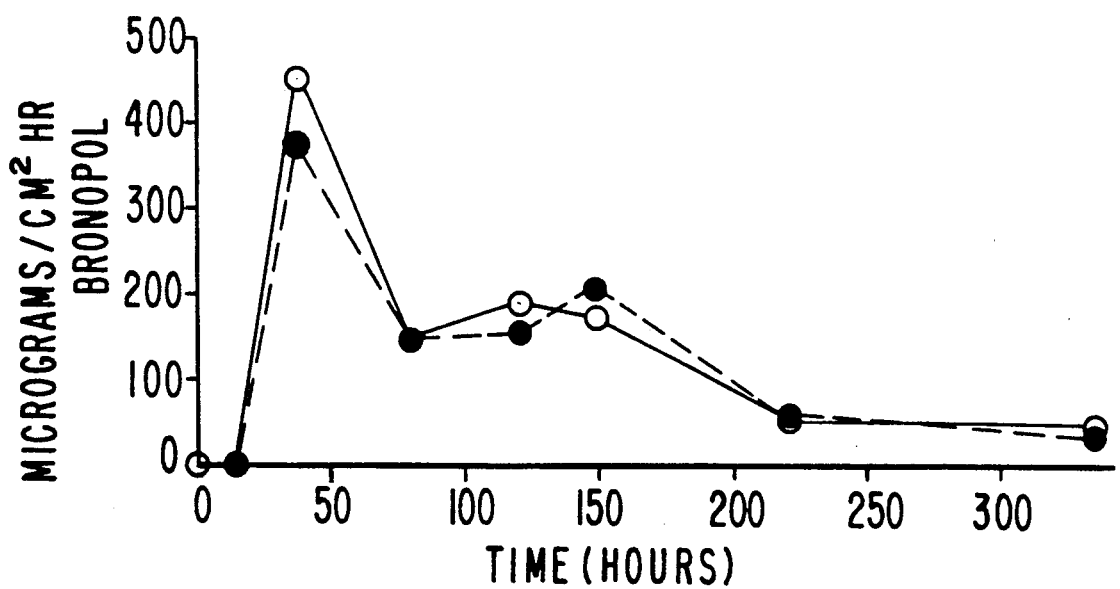
Figure 8:
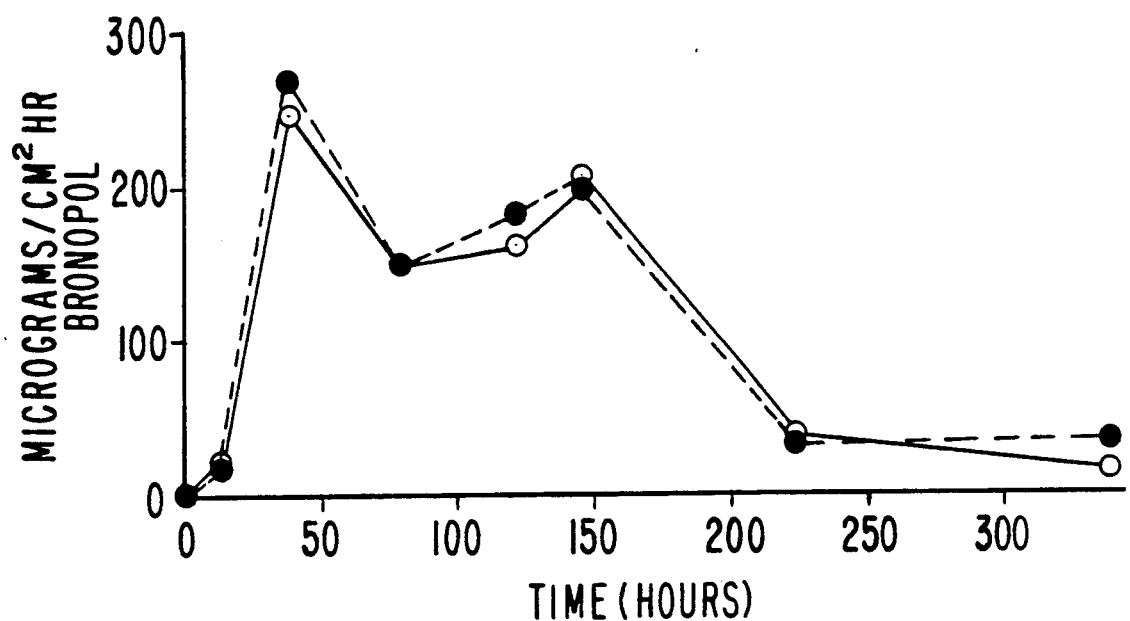

FIG. 6 is an enlarged, fragmentary sectional view of the drainage container delivery device assembly of FIG. 2, taken through 4—4 of FIG. 2, for depicting an external delivery device pouch containing a biocide of a delivery device detachably positioned on an outside surface of the container; and, FIG. 7 and FIG. 8 depict the amount of a biocide that passes through the wall of a urinary container over time.

Figure 9:
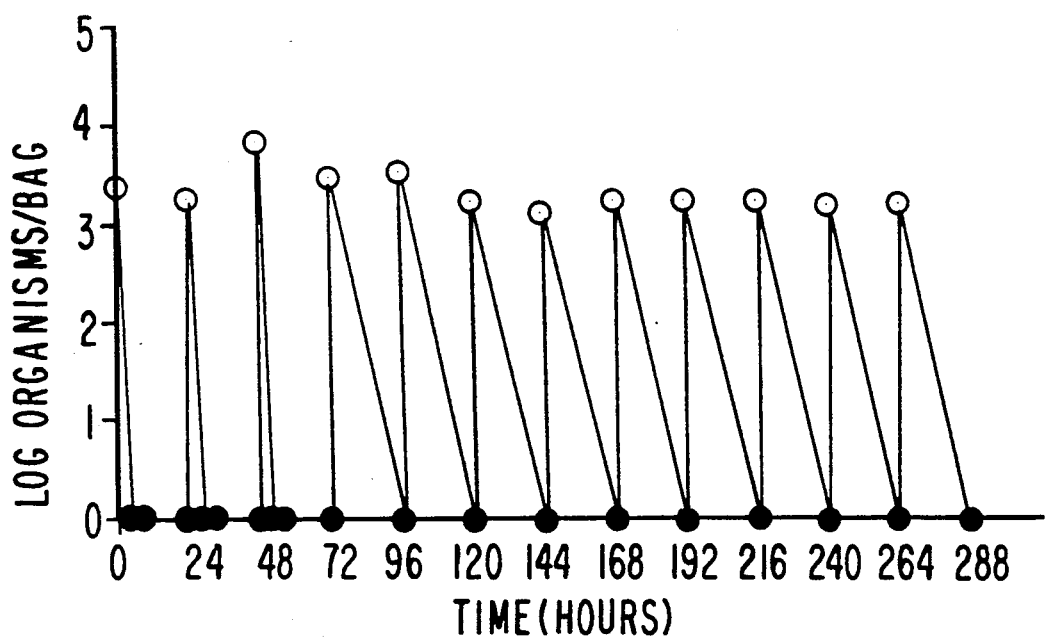

FIG. 9 depicts the effects of releases biocide on a pathogen over time.

Figure 10:
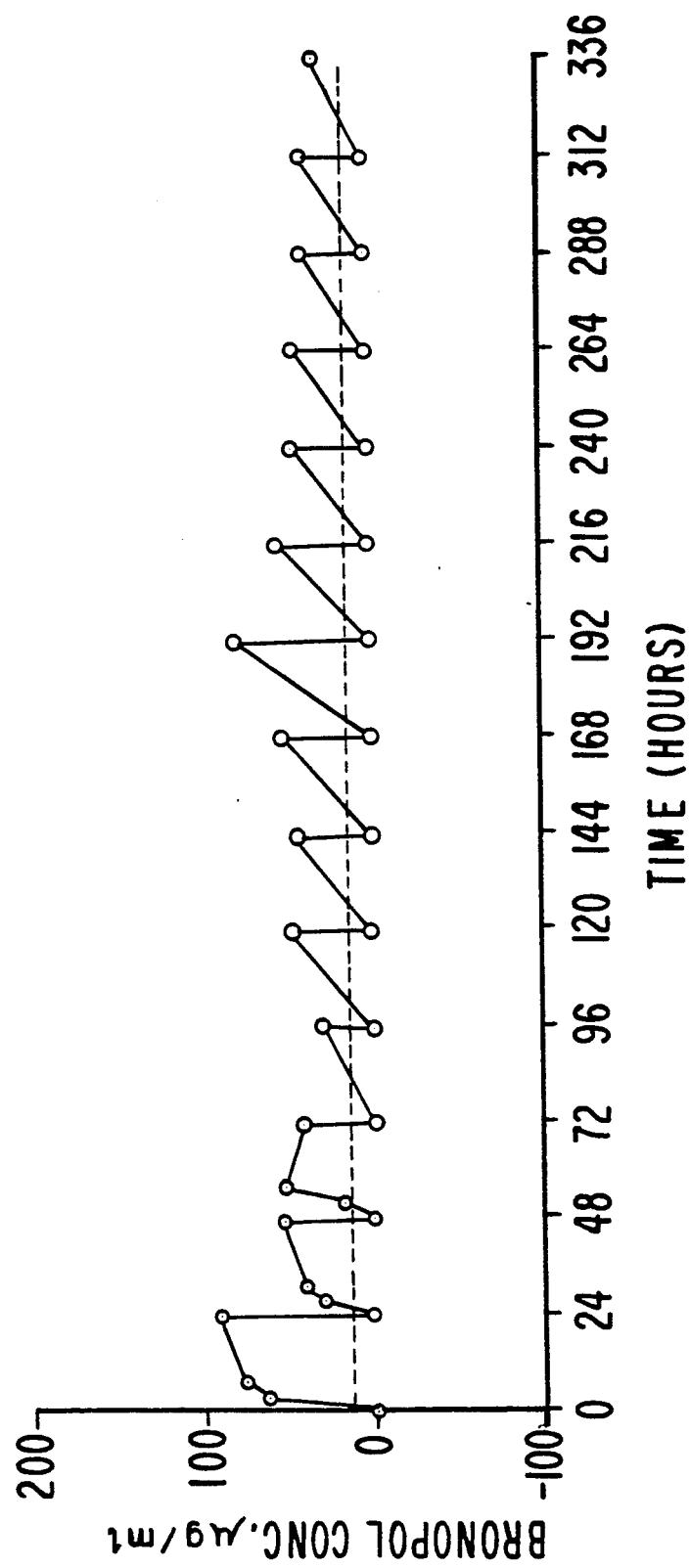

FIG. 10 shows the concentration of a biocide in the urinary drainage bag over time.

While the drawing figures illustrate various embodiments that can be made according to the invention, it is to be understood these embodiments are not to be limiting, as the embodiments can take a wide variety of shapes, sizes and forms adapted for delivering a biocide into a container for the intended purpose.

In the specification and in the drawing figures, and like parts in related figures are identified by like numbers. The terms appearing earlier in the specification and in the drawing figures, as well as embodiments thereof, are further discussed elsewhere in the disclosure.

DETAILED DISCLOSURE OF THE DRAWING FIGURES

Figure 1:
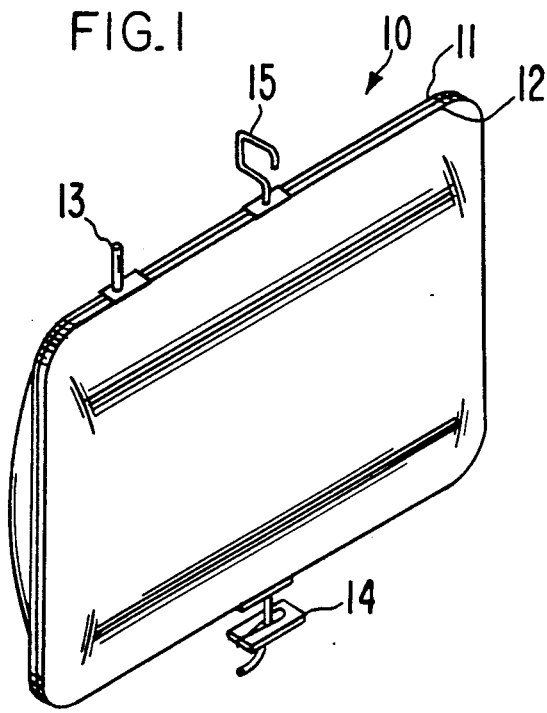
FIG. 1 is a partially exposed view of a urinary collection container used for the purpose of this invention.

Turning now to the drawing figures in detail, which are example of various embodiments of the invention, and which examples are not to be construed as limiting the invention, one embodiment of a urinary drainage container as indicated in FIG. 1 by the number 10. In FIG. 1, there is illustrated one embodiment of a bedside draining container 10 designed for use in a closed catheter system. In one preferred manufacture bedside draining bag 10 is made from two films of plastic 11 and 12, such as polyvinyl chloride. The two films are sealed to each other around their peripheral edges, for example by an electronic welding procedure, or they can be heat sealed to each other to provide a sealed container 10. Optionally, one wall, or both walls comprising container 10 may be transparent or translucent for exposing the contents of the container. In one presently preferred embodiment, the wall is made opaque by the addition of $TiO_2$. In another manufacture both walls 11 and 12 can comprise a composition that is substantially impermeable to the passage of a biocide, or in another manufacture, at least one wall comprises a composition permeable to the passage of a biocide by diffusion. Drainage container 10 preferably is manufactured as a bag, usually flexible, and it is provided with an inlet fitting 13 for receiving a catheter for letting fluid flow into the container. Drainage container 10 also is provided with a drainage assembly 14 for periodically draining the contents of the container. A hook 15 is fixed to the top of container 10 for hanging the container on a beside stand.

In FIG. 1, container 10 is illustrated in an essentially closed or flat state. Container 10, when put into use, generally is free of air at the beginning of receiving fluid from a patient. Over time, as fluid drains into container 10, flexible walls, 11 and 12 bulge outward, thereby increasing the space inside the container for receiving an increasing volume of urine. In another embodiment container 10 may be manufactured as a bag comprising a flexible polymeric composition. Container 10, when made as a bag, can be produced by blowing an extruded tube of the polymeric composition to conform to the interior of a mold cavity having the desired configuration.

In a presently preferred embodiment at least one of wall 11, or wall 12, or both wall 11 and wall 12, are made from a polymeric composition that permits the passage of a biocidal agent from an outside delivery source through wall 11 or wall 12 into the inside of container 10. In another presently preferred embodiment, at least one of wall 11, or wall 12, or both wall 11 and wall 12 are made from a polymeric composition that is substantially impermeable to the passage of biocide. In this latter embodiment, a biocidal delivery device positioned on the outside of a wall delivers the biocide and the device also delivers a plasticizer or a flux enhancer, or both that contact and permeate into the wall to make it permeable to biocide or to transport a biocide through the wall. Representative polymeric compositions for forming walls 11 and 12 comprise olefin polymers, vinyl polymers, condensation polymers, addition polymers, rubber polymers and silicon polymers. More specific polymers comprise a member selected from the group consisting of polyethylene, polypropylene, polyvinyl acetate, polyvinyl acetate, polyvinyl chloride, polyamide, polyester, butadiene rubber and organo-silicon polymers, and the like.

The plasticizers that can be used for the purpose of this invention comprises plasticizers that, when added to a wall-forming composition or diffused into a wall, for softening the wall, increasing its flexibility, and its permeability to the passage of a biocide. The plasticizers generally comprise, in a presently preferred embodiment, a member selected from the group consisting of monoglycerides, diglycerides, triglycerides, phthalate esters, di-2-ethylhexyl phthalate, butyl phthalate, dibutyl phthalate, diamyl phthalate, ethyl phthalate, alkyl phthalate, dialkyl phthalate, dioctyl phthalate, dibutyloxyethyl phthalate, dimethyl phthalate, diphenyl phthalate, diethyl phthalate, dicyclohexyl phthalate, di(methoxyethyl) phthalate, methyl phthalate, ethyl phthalate, benzyl phthalate, methylglycol phthalate, alkyl glycolate, butyl glycolate, ethyl glycolate, dibutyl succinate, diethyl succinate, diethylene glycol dipropionate, trialkyl esters of acyl citric acid, triethyl citrate, tributyl citrate, acetyltriethyl citrate, acetyltributyl citrate, trimethyl citrate, acetyltri-n-hexyl citrate, n-butyltri-n-hexyl citrate, tricyclohexyl citrate, acetyltri-n(hexyl/oct/decyl) citrate, acetyltri-n-(octyl/decyl) citrate, citric acid esters, tristearyl-citrate, acetyltri-n-(decyl/dodecyl) citrate, acetyl tri-2-ethylhexyl citrate, tributyl phosphate, alkyl-aryl phosphates, trimethyl phosphate, triethyl phosphate, cresyldiphenyl phosphate, triethylene glycol dibutyrate, glycol monooleate, polyethylene glycol-200, polyethylene glycol 400, propylene glycol, ethylene glycol 400, propylene glycol, ethylene glycol monoacetate, dialkyl adipates, dialkyl sebacates, diethyl tartrate, dibutyl tartrate, dibutyl sebacate, dibutyl maleate, fatty acid ester derivatives, ethylene glycol diacetate, dioctyl adipate, di-n-hexylazelate, butyl stearate, diethyl oxalate, di-isodecyl adipate, di(2-ethylhexyl) adipate, diethyl lauramide, fatty acid esters of polysaccharides, natural glycerides of unsaturated fatty acids, glycerin, monacetin, diacetin, triacetin, soybean oil exposide, stearyl citrate, methylglycol stearate, tri(n-octyl/n-decyl) trimellitate, triisodecyl trimellitate, tri-n-hexyl trimellitate, di(2-ethylhexyl) isophthalate, butyl ricinoleate, natural oils, derivatives of natural oils, oleic oil, mineral oil, fish oil, lard oil, vegetable oil, babassu oil, castor oil, coconut oil, cottonseed oil, corn oil, linseed oil, olive oil, palm oil, peanut oil, safflower oil, sesame oil, soybean oil, tall oil, linoleic acid, butyl stearate, benzyl benzoate, silicone oil, hydrogenated oil, methyl ester of rosin stearic acid, cityl alcohol, acetylated glycerides, glycol esters, and the like. The amount of plasticizer manufactured into a wall in a presently preferred embodiment is from 0.01 weight percent (wt %) to 30 wt % or more. The amount of plasticizer in a preferred embodiment when present in a biocidal dispensing device is from 0.01 wt % to 20 wt %, or more.

The flux exhancer present, in a preferred embodiment, is a delivery device for transporting or carrying a biocide from the device and through a wall of a urine container. The flux enhancer comprises a composition that promotes the amount of biocide transported per unit time through a wall of a container. The flux or transporting enhancer suitable for the purpose of the invention includes monovalent, unsaturated and saturated aliphatic, cycloaliphatic, and aromatic alcohols comprising from 1 to 18 carbon atoms, such as methyl alcohol, ethanol, hexanol, and the like; aliphatic, cycloaliphatic and aromatic hydrocarbons comprising from 2 to 18 carbons such as hexane, hexane, cyclohane, isopropylbenzene and the like; aliphatic, cycloalphatic and aromatic aldehydes and ketones comprising from 4 to 18 carbons, such as heptylaldehyde, cyclohexanone and benzaldehyde, and the like; aliphatic, cycloaliphatic and aromatic esters comprising from 4 to 18 carbons atoms such as isoamylacetate and benzylpropionate, and the like; acetamides; N,N-di(lower) alkyl acetamides such as N,N-dietyl acetamide, N,N-dimethyl acetamide, N-(2-hydroxyethyl) acetamide and the like; halogenated aliphatic, cycloaliphatic and aromatic flux enhancers;

nitrated aliphatic, cycloaliphatic and aromatic flux enhancers; and the like. The amount of flux enhancer presently preferred in a biocidal dispensing device is from 0 wt %, usually 0.01 wt % to 15 wt %, or more. In an optional embodiment provided by the invention, the biocidal delivery device can comprise a biocide and a plasticizer and a flux enhancer for providing the intended results.

FIG. 2 illustrates a urinary drainage container 10 comprising a wall 11, a wall 12, an inlet 13, an outlet port 14, a hook 15, and a biocidal delivery device 16 positioned on the outside wall 12 of container 10. Delivery device 16 can be placed at any position on the outside of the container, usually near the bottom. Also, delivery device 16 can be positioned vertically on the outside wall of container 10.

Figure 3:
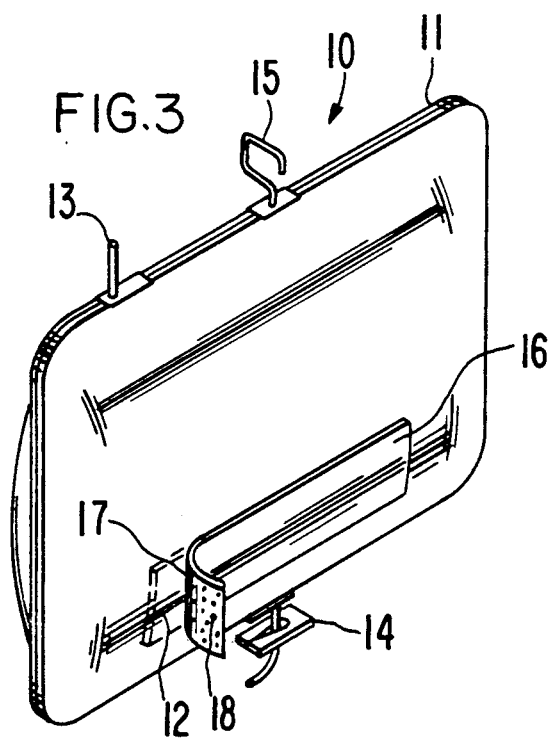
FIG. 3 is a side view of a urinary drainage container depicting a dispensing device in partially opened, peeled-back configuration, positioned on the exterior surface of the container.

FIG. 3 depicts the urinary drainage container 10 of FIG. 2 comprising wall 11, wall 12, inlet port 13, outlet port 14, hanging hook 15 and biocidal delivery device 16 mounted onto an external surface of wall 12 of container 10. In FIG. 3, delivery device 16 is peeled-open at 17 for illustrating delivery device 16 comprising biocide 18 in delivery position on wall 12. Delivery device 16, in one embodiment, is a reservoir formed of a polymeric composition comprising a biocide agent 18. The polymer composition stores and releases a biocide 18 by diffusion or by osmotic action to wall 12. Representative polymers comprising delivery device 16 comprise a homopolymer, copolymer, cross-linked polymer, diffusion polymer, a microporous polymer, or the like. Examples of polymers include acrylic polymers and copolymers of methacrylate, ethyl acrylate, ethyl methacrylate, and methylmethacrylate; homopolymers and copolymers including vinyl chloridevinylacetate copolymer; chlorinated vinyl chloride; polyethylene; polypropylene; ethylene propylene copolymer; chlorinated polyethylene; ethylenevinylacetate copolymer; styrene-butadiene copolymer; acrylonitrile-styrene-butadiene terepolymer; polyvinylidene chloride; vinylchloride acrylonitrile copolymer; vinylchloride-vinylidene chloride copolymer; vinylidenechloride-acrylate ester copolymer; polybutylene terephthalate; vinyl chloride-acrylate ester copolymer; cross-linked polyvinyl acetals such as cross-linked polyvinyl formal cross-linked polyvinyl acetal and cross-linked polyvinyl butyral; polyethers; polyesters; sparingly cross-linked polyesters; polyurethane; polyamide; chlorosulfonated polyolefins; polyolefins; polybutadiene; polyisoprene; polysilicon; and the like. The polymers are known in *The Handbook of Common Polymers*, by Scott et al., (1971), published by CRC Press, Cleveland Ohio; in *Modern Plastics Encyclopedia*, (1979), published by McGraw-Hill Inc., New York, N.Y.; and in *Handbook of Plastics and Elastomers*, by Harper, (1976), published by McGraw-Hill Inc. San Francisco, Calif.

The biocides 18 useful for incorporating in device 16 for the purposes of the invention include a biocide member selected from the group consisting essentially of a phenol, quaternary ammonium biocides, surfactant biocides, chlorine-containing biocides, quinoline, quinaldinium, lactone, antibiotics, dye, thiosemicarbazone, quinone, sulfa, carbamates, urea, salicylamide, carbanilide, amide, guanide, amidine, chelate and imidazoline biocides.

Exemplary biocides 18 dyes include acridine, acriflavine, aminacrine hydrochloride, proflavin hemisulfate, triphenylmethane, magenta, crystal violet, scarlet red, pararosaniline, and rosaniline. Exemplary chlorine releasing biocides include sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated diaklyl-hydantoin, and halane.

Examples of quinaldinium and quinoline biocides 18 are dequalinium, laurolinium, hydroxyquinoline, lioquinol, chlorquinaldol and halquinol. Exemplary quaternary ammonium biocides include pyridinium biocides, benzalkonium chloride, cetrimide, benzethonium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride ortaphonium chloride, and triclobisonium chloride. Exemplary furans include greseofulvin, nitrofurfural, nitrofurazone, nitro-furantoin, furazolidone, and furaltadone.

Exemplary phenol biocides 18 include a member selected from the group consisting essentially of chlorinated phenol, cresol phenol, thymol, chlorocresol, chloroxylenol, hexachlorophane, bisphenols, amylmetacresol, bithionol, chlorothymol, dichloroxylenol, chlorophene, p-chlorophenol, p-phenylphenol, trinitrophenol, dichlorobisphenol, and bromochlorobisphenol. Exemplary antibiotics include penicillins, gentemyctin, aminoglycosides, benzylpenicillin, ampicillin, tetracylines, cephalosporins, neomycin, chloramphenicol, vancomycin, fudicin, rifampicin, cephaloridine, erythromycin, actinomycin, neomycin, polymyxin, colistin, gentamicin, bactriun, carbenicillin and streptomycin. Exemplary lactones include propiolactone. Exemplary urea biocides include noxytiolin, polynoxylen and triclocarbon.

Examples of other biocides 18 useful for the purpose of the invention are chlorhexidine gluconate, chlorhexidine, chlorhexidine acetate, chlorhexidine hydrochloride, dibromopropamide, halogenated diphenylalkanes, cibromsalan, metabromsalan, tribromsalan, carbanilide, salicylanilide, tetrachlorosalicylanilide, trichlorocarbanilide, propamide isethionate, pentamidine, picloxydine, mendalamine, methenamine salts, the acid addition and quaternary, methenamine mandelate, polyoxmethylene esters such as polyoxmethylene diester, polyoxmethylene diacitate, and the like and mixtures thereof. A presently preferred biocide 18 is bronopol. The concentration of biocide 18 in device 16 generally is about 0.1% to 80% by weight, with a more presently preferred amount of 5% to 50% by weight. Device 16 in a preferred manufacture can be made for releasing anti-infective amounts of biocide 18 over a prolonged period from several hours to 30 days or longer, with a more preferred period of 1 to 14 days. The devices of the invention release from 10 ng to 750 mg per hour, or higher. One device can be used at a time, or two or more devices can be used at a time. The devices can be used in succession, and more than one device can be used simultaneously.

The rate of diffusion of a biocide, a flux enhancer, or a plasticizer through a wall can be determined by standard procedures. In this manner, particular materials used as the walls of a urine receiving container can be selected for the intended purpose. Various techniques, such as the transmission method, the sorption/desorption method, and the like, can be used as measures of permeability. One presently preferred technique that has been found to be eminently well-suited is to cast or hot press a film of the material to a thickness of about 1 to 1 to 60 mils. The film is used as a barrier between a rapidly stirred (e.g. 150 rpm) biocide and/or flux enhancer saturated solution and water of a constant temperature (typically 25° C.). Samples are periodically withdrawn from the solvent bath and analyzed for biocide concentration. By plotting the biocide concentration in the solvent bath, versus time, the permeability constant P of the material is determined by Fick's First Law of Diffusion, using the following equation:

$$\text{Slope of plot} = (Q_2 - Q_1)/(t_2 - t_1) = PAC/h,$$

wherein:

$Q_1$ = cumulative amount of biocide in receptor solvent at $t_1$ $Q_2$ = cumulative amount of biocide in receptor solvent at $t_2$ $t_1$ = elapsed time to first sample, i.e., $Q_1$ $t_2$ = elapsed time to second sample, i.e., $Q_2$ $A$ = area of membrane in cm$^2$ $C$ = initial concentration of biocide $h$ = thickness of membrane in cm By determining the scope of the plot, i.e., $(Q_2-Q_1)/(t_2-t_1)$ and solving the equation using the known or measured values of A, C, and h, the permeability P constant in cm$^2$/time of the material for a given biocide is readily determined.

The release rate through different biocide release controlling materials can be easily ascertained by standard techniques known to the art as recorded in *J. Pharm. Sci.*, Vol. 52, pp 1145-1149, (1963); ibid., Vol. 53, pp 798-802, (1964); ibid., Vol. 54, pp 1459-1464, (1965); and ibid., Vol. 55, pp 840-843 and 1224-1239, (1966); *Encycl. Polymer Sci. Technol.*, Vols. 5 and 9, pp 65-82 and 794-807, (1968) and the references cited therein, in U.S. Pat. Nos. 3,845,480; 3,845,761, 3,896,819; and 4,853,229.

The biocides kill, prevent or retard the presence of harmful or unwanted microorganisms inside a urine container. Typical microorganisms include the fungi *Aspergillus niger, Aspergillus flavus, Rhizopus nigricans, Cladosporium herbarium, Epidermophyton floccosum, Trichophyton mentagrophytes, Histoplasma capsulatum,* and the like. The term, "micro-organisms," also includes *Psuedomonas aeruginosa, Escherichia coli, Proteus vulgaris, Staphyloccus aureus, Streptococcus faecalis, Klebsiella, Enterobacter aerogenes, Proteus mirabilis,* other gram-negative bacteria and other gram-positive bacteria, mycobactin, and the like. The term also embraces yeast such a *Saccharomyces cerevisiae, Candida albicans,* and the like. Additionally, spores of microorganisms, viruses and the like, are within the intent of the invention. The biocides are disclosed in *Disinfection, Sterilization and Preservation,* by Block, (1977), published by Lea & Febiger, Philadelphia, Pa.; in *Inhibition and Destruction of Microbial Cells,* by Hugo, (1971), published by Academic Press, New York, N.Y.; in *Martindale The Extra Pharmacopoeia,* edited by Blacow, published by The London Pharmaceutical Press, London; and in U.S. Pat. No. 4,445,889.

Delivery device 16 can be held, releasably or permanently, on the outside wall of a drainage container by an adhesive. Representative adhesives include a mixtures of 2-cyanoacrylate and dimethyl methylenemalonate, monomeric ester of alpha-cyanoacrylic acid, cross-linked copolymer of dimethylaminoethylmethacrylate and an alkyl scrylate, adhesive composition comprising a hydrocolloid gum, polyisobutylene and cross-linked dextran, silicon medical adhesive, mineral oil polyisobutylene adhesive, and the like. The adhesive optionally can contain a rheological agent that imparts thixotropic characteristics to the adhesive, that aids in increasing its cohesiveness and bond strength, imparts slump control, maintains the delivery device on the container, and lets it be easily removed therefrom at the end of the delivery period. The rheological agents useful for this purpose are silicone compounds such as fumed silica. These adhesives can be applied directly on the biocide releasing surfaces of device 16 or used as an adhesive layer in the overlay adhesive which is placed over the entire device 16, in order to secure the device on the urinary bag walls.

Figure 4:
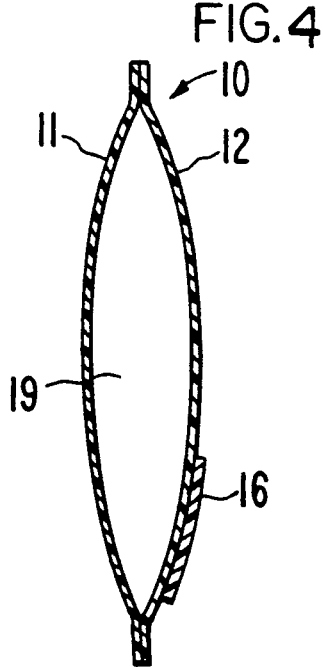
FIG. 4 is an enlarged, fragmentary sectional, side view of the drainage container delivery device assembly of FIG. 2, taken through 4—4 of FIG. 2.

FIG. 4 is a sectional view through 4—4 of FIG. 2. In FIG. 4, there is illustrated urinary drainage container 10, comprising two walls, wall 11, and wall 12, and a delivery device 16 positioned on outside of wall 12, for supplying a biocide to lumen 19 the inside of drainage container 10.

Figure 5:
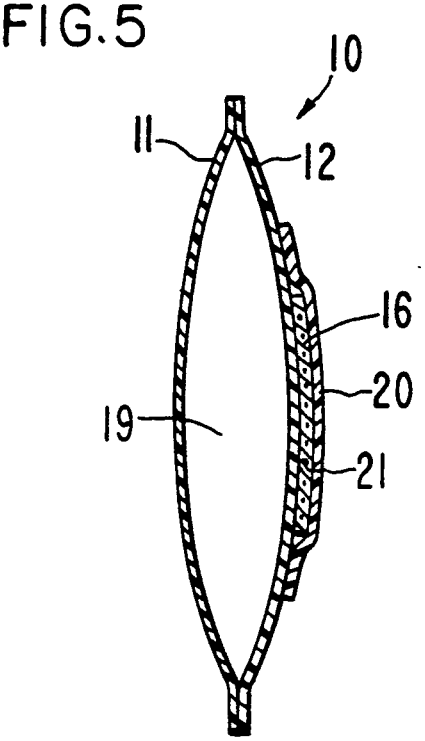
FIG. 5 is an enlarged, fragmentary sectional, side view of the drainage container delivery device assembly of FIG. 2, taken through 4—4 of FIG. 2, for depicting an external delivery device comprising a backing member and a reservoir optionally releasably positioned on the outside wall of a drainage container.

FIG. 5 is a sectional view through 4—4 of FIG. 2. In FIG. 5, there is illustrated urinary drainage container 10 comprising wall 11, wall 12, lumen 19, and delivery device 16. In FIG. 5, delivery device 16 is covered or laminated with a membrane 20 that is substantially impermeable to the passage of biocide 21 in device 16. The presence of impermeable membrane 20 insures unidirectional passage of biocide 21 through wall 12 into lumen 19. Backing member 20 preferably comprises occlusive, nonocclusive, flexible and non-flexible materials. Examples of materials that can be used for backing member 20 include high density polyethylene, metal foil used alone, such as aluminum, or metal foil laminated to a polymeric substrate for added strength and toughness. In one preferred embodiment backing member 20 is a composite designed for strength and as a barrier for preventing loss of biocide 21. Multilaminated films also can serve as a backing member comprising a lamina of medium density polyethylene in laminar arrangement with a lamina comprising a polyethylene terphthalate on which a thin layer of aluminum was vapor deposited. Siliconized polymers, such as siliconized polyalkylene terephthalate also can be used alone, or in a laminate. In an optional embodiment, not shown, external delivery device 16 can comprise a multilaminate, or a form fill and seal delivery system.

FIG. 6 is a sectional view through 4—4 of FIG. 2. In FIG. 6, there is seen urinary drainage container 10 comprising a single film container comprising with a first wall surface 11, and a second wall surface 12, an internal lumen 19 and an external delivery device 22 positioned on the outside surface of container 10. Delivery device 22 is sized, shaped and adapted as an external pouch. External pouch device 22 comprises a wall 23 that defines an internal space 24 in cooperation with the outer surface wall 12 of container 10. Wall 23 of pouch device 22 comprises a composition that is substantially impermeable to the passage of a biocide 25 in space 24. The pouch 22 comprises internally at least in part a biocide 25, or the pouch is filled with biocide 25, which is available for passage through wall 12. Pouch 22 comprises an injection port 26 for filling and refilling reservoir space 24. The biocide 25 can be present in any form that readily makes available biocide 25 to wall 12. Exemplary biocide 25 releasing forms comprise a member selected from the group consisting of solid, crystalline, microcrystalline, particle, pellet, granule, powder, tablet, spray-dried, lyophilized, or compressed forms that release the biocide, such as, a compressed powder, compressed granules, and the like. The biocide can be mixed with a carrier such as silicone oil, mineral oil, rapeseed oil, palm oil, agar-agar, sodium alginate, gum Arabic, methyl cellulose, silica gel, and the like. External pouch 22 can also comprise a biocidal emulsion, a biocidal suspension, an optical permeation enhancer such as glyceryl monooleate, dimethyl sulfoxide, ethanol, and the like, for transporting a biocide through wall 12 of container 10; and the like. The amount of biocide 25 housed in internal space 24 is about 0.01 milligram to 25 grams, and the like.

DISCLOSURE OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawing figures, and the accompanying claims.

EXAMPLE 1

The delivery of the biocide bronopol from an external delivery pouch is seen from the following study: first, 40 mg per ml of bronopol was blended with 5 ml of a biocidal carrier comprising 2.5 ml of tributyl citrate and 2.5 ml of mineral oil and the blend charged into an external, adhesively positioned device on the outside surface of a urinary drainage bag. The bag was made of opaque polyvinyl chloride with a wall thickness of 10 mils, and the bag had an internal lumen of 25 ml. The bronopol delivery rate through the wall of the bag is seen in FIG. 7 and in FIG. 8. In FIG. 7, the clear circle and the darkened circle represent the results of two separate studies. In FIG. 8 the delivery rate of bronopol is depicted through a 9 mil opaque or white polyvinyl chloride wall into a bag having a fluid receiving volume of 25 ml. The bronopol was in a carrier as a concentration of 40 mg/ml, which carrier comprises of 2.5 ml of tributyl citrate and 2.5 ml of mineral oil, and the area of the wall through which the bronopol passed was 7.07 $cm^2$. The clear circles and the darkened circles represent the results of the two studies.

EXAMPLE 2

An experiment was performed to determine both the minimum inhibiting concentration, MIC, and the minimum bactericidal concentration, MBC, of bronopol against E. coli, P. aeruginosa, S. aureus and C. albicans at 37° C. The initial colony forming unit per test tube ranged from 30 to 450, which was inoculated in actual human urine whose pH was approximately 6. The MIC values were from 12.5–25 μg/ml, and the MBC ranged from 25–50 μg/ml irrespective of the microorganisms tested. From this microbiological potency data, for an average daily urine output (2000 ml), and the size of a bronopol releasing system (50–100) $cm^2$, a determination was made of the required bronopol flux for biocidal control through the walls of urine bag made of poly(vinyl chloride), (PVC). The minimum bactericidal flux presently preferred is about 20 –40 μg/$cm^2$hr, which can be accomplished with the bronopol formulation used for the data shown in FIG. 7 and FIG. 8. The required, minimum inhibitory flux is approximately 10–20 μg/$cm^2$hr. According to FIGS. 7 and 8, the required bronopol flux for minimum inhibiting concentration (MIC) was continuously maintained for 7 to 14 days, or longer.

EXAMPLE 3

A biocidal delivery device is prepared by casting a film from a solution comprising 20 parts of polyisobutene having a 1,200,000 viscosity average molecular weight; 30 parts of polyisobutene having a 35,000 viscosity average molecular weight; 40 parts of mineral oil; and, 10 parts of bronopol in chloroform solvent cast onto an biocidal impermeable film of aluminized polyethylene terephthalate. A contact adhesive is applied around the edges of the film comprising the bronopol. A reservoir-backing member is applied to the opaque, outer surface of a urinary drainage bag for delivering the biocide to the inside of the bag over a prolonged period of 360 hours.

EXAMPLE 4

A delivery system for evaluating the antimicrobial activity of bronopol against *Pseudomonas aeruginosa* was made comprising a releasing surface of 100 $cm^2$ comprising bronopol/citroflex-4 (30/70) and it was applied to the exterior surface of a urinary drainage bag. A separate urinary drainage bag served as a control. A sterile synthetic urine solution was infused independently into each urinary drainage bag at approximately 1.25 ml/mm for 14 days. During this time the bags were regularly drained and challenged with *Pseudomonas aeruginosa*, (approx. $10^3$ per challenge) at 24 hour intervals. Samples were removed at 4, 8, and 24 hours on the initial three days and at 24 hours intervals thereafter from the drainage bags for determination of viable organisms, as well as the dissolved bronopol concentration. The delivery device was applied to the exterior of the urinary drainage bag eleven days prior to the initiation of the test. In operation, the delivery system reduced the bacterial challenge below the limits of detection for twelve days, an eight log reduction compared to the control bag. In the last two days, the delivery device successfully reduced the proliferation of *Pseudomonas aeruginosa* by greater than 6 logs as compared to the untreated control bag. The bronopol concentration in the delivery device exhibited an initial concentration of 90.4 μg/ml and reduced to an average of 48.4 μg/ml for days 2 through 11 and ended with an average 34.3 μg/ml for days 12 through 14.

The *Pseudomonas aeruginosa* was inoculated from a stock culture into 25 ml of synthetic urine and incubated at 20°–25° C. for 24 hours. Five consecutive transfers of 1 ml of a 24 hour culture (approx. $10^8$ cells) into 25 ml of synthetic urine were made prior to the start of the experiment.

The synthetic urine was prepared in two separate solutions, which were then combined into a single solution. One portion containing dextrose, magnesium sulfate, and urea were made and then filtered through a 0.2 μm filter. The remaining constituents of the synthetic urine were made in specified concentrations and autoclaved for 17 minutes at 121° C. and 15 psi pressure. The two separate portions were combined to provide a synthetic urine of the following formulation:

| Constituent | Concentration (grams/liter) |
| --- | --- |
| $K_2HPO_4$ | 4.0 |
| $Na_2HPO_4$—$7H_2O$ | 2.68 |
| $NaH_2PO_4$—$H_2O$ | 1.62 |
| $C_6H_5Na_3O_7$—$2H_2O$ (sodium citrate) | 1.0 |
| NaCl | 5.3 |
| $MgSO_4$—$7H_2O$ | 1.54 |
| $C_6H_{12}O_6$ (dextrose) | 0.83 |
| $(NH_2)_2CO$ (urea) | 18.0 |
| $(NH_4)_2SO_4$ | 1.2 |

The bronopol concentration in $\mu g/ml$ in a urine bag comprising the external delivery device and prepared according to the example is set forth in the following table:

| DAY | Bronopol Concentration ug/ml | | |
| --- | --- | --- | --- |
| | 4 HRS | 8 HRS | 24 HRS |
| 1 | 62.4 | 75.8 | 90.4 |
| 2 | 28.6 | 39.6 | 52.4 |
| 3 | 17.6 | 51.2 | 40.4 |
| 4 | | | 28.60 |
| 5 | | | 45.40 |
| 6 | | | 42.20 |
| 7 | | | 53.60 |
| 8 | | | 80.00 |
| 9 | | | 54.00 |
| 10 | | | 44.20 |
| 11 | | | 43.40 |
| 12 | | | 37.00 |
| 13 | | | 36.60 |
| 14 | | | 29.40 |

Accompanying FIG. 10 depicts a 14 day bronopol concentration in the urine drainage bag delivered from an exterior mounted delivery device of 100 cm² bronopol/citroflex-4 (30/70). In FIG. 10, the dotted line is the limit of detection of 12 $\mu g/ml$ and the line connected by clear circles is the bronopol concentration in the urine. Accompanying FIG. 9 depicts the biocidal efficacy of a bronopol/citroflex-4 (30/70) device on the exterior of the urine bag against *Pseudomonas aeruginosa* in the urine bag. The clear circle denotes the inoculation concentration of *Pseudomonas aeruginosa* and the black circles indicate the concentration determined in 24 hours.

EXAMPLE 5

An external delivery device comprising bronopol and a flux enhancer ethanol is prepared according to the above examples. The codifussion of bronopol and ethanol effect the delivery of bronopol through a urine bag wall comprising a wall free of plasticizer, or comprising a plasticizer for delivering bronopol into the urine bag.

DISCLOSURE OF MODES OF PERFORMING THE INVENTION

The invention pertains also to a method for admitting a biocide into a urine bag for substantially preventing, reducing or eliminating the presence of pathogens in the urine bag, wherein the process comprises: (1) placing a biocidal delivery device on the exterior surface of a urine container, said delivery device comprising (a) a reservoir comprising a composition in contact with the wall of the urine container; (b) about 0.1% to 80% by weight of a biocide in the reservoir, which biocide is delivered at a rate of 10 ng to 750 mg per hour through the wall into the container for substantially preventing, reducing or eliminating the presence of pathogens inside the container for a prolonged period of time up to 30 day; (c) a backing member in contact with the other surface of the reservoir, the backing member comprising a composition substantially impermeable to the passage of biocide; (2) releasing the biocide from the reservoir; and, (3) diffusing the biocide through at least one wall of the container to produce the desired effects in the urine container. The method also comprises using a device comprising a plasticizer, or a flux enhancer, or both for modifying the permeability of the wall and for increasing the flux of the biocide.

It will be understood by those versed in the medical, surgical and patient-care arts that in the light of the present specification, drawings and the accompanying claims, this invention makes available to the art both a novel and useful delivery device and a combination dispensing device and container endowed with beneficial properties. It will be further understood by those versed in the art that many embodiments of this invention can be made without departing from the scope of the invention. Accordingly, it is to be understood the invention is not to be construed as limited, but it embraces all equivalents inherent therein.

We claim:

1. An apparatus comprising, in combination:

(a) a container comprising a lumen for receiving a biological fluid, the container comprising:
  (i) a wall that surrounds the lumen;
  (ii) an inlet port for letting a fluid into the container;
  (iii) an outlet port for letting fluid leave the container; and,
(b) a delivery device on the outside of the container, the device comprising:
  (iv) a reservoir in contact with the container, said reservoir comprising a polymeric composition;
  (v) a biocide in the reservoir;
  (vi) a plasticizer in the reservoir; and
  (vii) a backing member in contact with the reservoir, the backing member comprising a composition substantially impermeable to the passage of a biocide.

2. The apparatus according to claim 1, wherein the biocide is bronopol.

3. An apparatus comprising in combination:

(a) a container comprising a lumen for receiving a biological fluid, the container comprising:
  (i) a wall that surrounds the lumen;
  (ii) an inlet for letting fluid enter the container; and,
  (iii) an outlet for letting fluid leave the container; and,
(b) a delivery device on the outside of the container, the delivery device comprising:
  (iv) a reservoir comprising a polymeric composition in contact with the container;
  (v) a biocide in the reservoir;
  (vi) a flux enhancer in the reservoir; and
  (vii) a backing member in contact with the reservoir, the backing member comprising a composition substantially impermeable to the passage of a biocide.

4. The apparatus according to claim 3, wherein the biocide is bronopol.

5. An apparatus comprising in combination:

(a) a container comprising a lumen for receiving a biological fluid, the container comprising:
  (i) a wall that surrounds a lumen;

(ii) an inlet port for admitting a fluid into the container;
(iii) an outlet port for draining the container; and,
(b) a delivery device on the outside wall of the container, the device comprising a release rate polymeric film comprising a biocide and a flux enhancer that are released by the film to the wall for passage into the container over time.

6. The apparatus according to claim 5, wherein the bicycle is bronopol.

7. An apparatus comprising in combination:
(a) a container comprising a lumen for receiving a biological fluid, the container comprising:
(i) a wall that surrounds the lumen;
(ii) an inlet port for admitting a fluid into the container;
(iii) an outlet port for draining the container; and,
(b) a delivery device on the outside wall of the container, the device comprising a release rate polymeric film comprising a biocide and a plasticizer that are released by the film to the wall for passage into the container over time.

8. The apparatus according to claim 7, wherein the biocide is bronopol.

9. An apparatus comprising in combination:
(a) a container comprising an internal space for receiving a biological fluid, the container comprising:
(i) a wall that surrounds the internal space;
(ii) an inlet port for letting fluid enter the space;
(iii) an exit for letting fluid exit the space; and,
(b) a delivery device on the outside of the container, the delivery device comprising:
(iv) a reservoir comprising a polymeric composition in contact with the container;
(v) a biocide, a plasticizer and a flux enhancer in the reservoir; and
(vi) a backing member in contact with the reservoir, the backing member comprising a composition substantially impermeable to the passage of the biocide, the plasticizer and the flux enhancer.

* * * * *